United States Patent
Chang

(10) Patent No.: US 7,751,604 B2
(45) Date of Patent: Jul. 6, 2010

(54) MEDICAL INTELLIGENT SERVER ARCHITECTURE

(75) Inventor: JaeJung Chang, Milpitas, CA (US)

(73) Assignee: Fujifilm Corporation, Tokyo (JP)

( * ) Notice: Subject to any disclaimer, the term of this patent is extended or adjusted under 35 U.S.C. 154(b) by 888 days.

(21) Appl. No.: 11/606,083

(22) Filed: Nov. 30, 2006

(65) Prior Publication Data

US 2008/0133596 A1 Jun. 5, 2008

(51) Int. Cl.
*G06K 9/00* (2006.01)
*G06F 17/00* (2006.01)
(52) U.S. Cl. .................... 382/128; 707/104.1
(58) Field of Classification Search ................ 382/128, 382/129, 130, 131, 132, 133, 134; 378/901; 600/300, 407, 410, 425; 707/104.1; 725/4, 725/82, 91, 96, 103; 128/920, 922
See application file for complete search history.

(56) References Cited

U.S. PATENT DOCUMENTS

| | | | |
|---|---|---|---|
| 6,289,115 B1 | 9/2001 | Takeo et al. | |
| 6,304,967 B1 | 10/2001 | Braddy | |
| 6,551,243 B2 | 4/2003 | Bocionek et al. | |
| 6,574,629 B1 | 6/2003 | Cooke, Jr. et al. | |
| 6,598,011 B1 | 7/2003 | Howards Koritzinsky et al. | |
| 6,603,494 B1 | 8/2003 | Banks et al. | |
| 6,678,703 B2 | 1/2004 | Rothschild et al. | |
| 6,678,764 B2 | 1/2004 | Parvulescu et al. | |
| 6,748,593 B1 | 6/2004 | Brenner et al. | |
| 6,779,182 B1 | 8/2004 | Zolnowsky | |
| 6,819,785 B1 | 11/2004 | Vining et al. | |
| 6,820,100 B2 | 11/2004 | Funahashi et al. | |
| 6,859,783 B2 | 2/2005 | Cogger et al. | |
| 6,922,724 B1 | 7/2005 | Freeman et al. | |
| 6,934,698 B2 * | 8/2005 | Judd et al. | 707/1 |
| 6,950,985 B2 | 9/2005 | Lee | |
| 6,965,938 B1 | 11/2005 | Beasley et al. | |
| 6,993,767 B2 | 1/2006 | Brenner et al. | |
| 7,016,952 B2 | 3/2006 | Mullen et al. | |
| 7,054,473 B1 * | 5/2006 | Roehrig et al. | 382/128 |
| 7,058,901 B1 * | 6/2006 | Hafey et al. | 715/792 |
| 7,059,721 B2 | 6/2006 | Hayashi et al. | |
| 7,062,105 B2 | 6/2006 | Funahashi et al. | |
| 7,080,095 B2 * | 7/2006 | Accardi et al. | 707/104.1 |
| 7,117,242 B2 | 10/2006 | Cherkasova et al. | |
| 2003/0002748 A1 | 1/2003 | Funahashi | |
| 2006/0115136 A1 | 6/2006 | Funahashi | |
| 2006/0142647 A1 | 6/2006 | Oosawa | |

* cited by examiner

*Primary Examiner*—Abolfazl Tabatabai
(74) *Attorney, Agent, or Firm*—Birch, Stewart, Kolasch & Birch, LLP

(57) ABSTRACT

Disclosed is medical intelligent server architecture for computer aided detection that is capable of scaling up for increasing number of patients, and that facilitates modifications and additions of detection services based on various modalities. The architecture is a dedicated server configuration capable of providing services for detecting diseases upon being provided a set of medical images. The architecture is capable of being integrated into existing medical information systems. The architecture for computer aided detection is adaptable to variations in demand for computer aided detection serves, is easily expandable to include new or modified detection services, and is scaleable to accommodate an increasing number of patients and patient images of various types.

8 Claims, 5 Drawing Sheets

| SERVICE NAME | SERVICE URL |
|---|---|
| ... | ... |

MEDICAL INTELLIGENT SERVER ARCHITECTURE

CROSS-REFERENCES TO RELATED APPLICATIONS

A related application Ser. No. 11/606,075 entitled "Job Dispatcher for Medical Intelligent Server Architecture," is being filed concurrently herewith, to JaeJung Chang, and is herein incorporated by reference.

BACKGROUND OF THE INVENTION

1. Field of the Invention

This invention relates to the art of medical computer aided detection, and more specifically, to computer aided detection based on a set of medical images.

2. Description of Related Art

Hospital information systems and medical laboratory systems are producing an increasing amount and types of medical image data. Hospitals have gradually replaced conventional clinical charts with electronic clinical charts. Hospitals have added databases of clinical histories and medical prescription histories. Radiology information systems have been added that provide information for aiding diagnosis. More recently, Picture Archiving and Communication Systems (PACS) have been developed as computer systems dedicated to the storage, retrieval, distribution and presentation of the medical image data. PACS are a replacement for hard-copy based means for managing medical images, such as film archives. Full PACS handle images from various modalities, such as ultrasonography, magnetic resonance imaging, position emission tomography, computed tomography, endoscopy, mammography and radiography (plain X-rays).

Computer aided detection (CAD) is currently proving to be an effective means of assisting doctors. For example, CAD has been useful in assisting doctors with patients having late stage illnesses. Algorithms for CAD are being developed and refined for an increasing number of diseases and illnesses.

A typical PACS network may consist of a central server which stores a database containing images. The central server may be connected to clients in a LAN or WAN, as well as over the Internet. Client workstations can include local peripherals for scanning image films into the system (e.g., film digitizer), printing image films from the system and interactive display of digital images. PACS workstations offer means of manipulating the images (crop, rotate, zoom, brightness, contrast, etc.).

Many types of imaging equipment, i.e. modalities, are becoming capable of feeding patient images directly to the PACS in digital form. A set of standards for storing and transmitting medical images have been developed known as Digital Imaging and Communications in Medicine (DICOM), a NEMA standard. DICOM has been developed to enable integration of scanners, servers, workstations, printers and network hardware from multiple vendors. Thus DICOM provides a common platform for a large number of modalities. DICOM includes both a file format definition and a network communications protocol for transmission of images.

The DICOM file format contains both a header and image data. The header can contain standardized fields and free-form fields. DICOM files contain required elements, which are dependent on the image type (i.e., corresponding to a modality).

A patient visit to a hospital or other medical practice can result in a study made including data obtained for a modality that may provide one or more image files. Several patient visits can result in several studies. A PACS system is typically capable of storing and managing image files for many patients. CAD algorithms are continuously being developed that can perform detection using medical images. However, there is a need for a system that can provide the large number of medical images of patients to the CAD algorithms to perform diagnosis. In particular, a system is desirable that can provide detection services for hundreds of patients, for many different potential diseases using an evolving variety of CAD software. Over a long term, a system serving such a role needs to adapt to a varying number and types of images and varying demand for detection services, be easily expanded to new or modified CAD software, and be capable of scaling up to handle an increasing number of patient studies.

BRIEF SUMMARY OF THE INVENTION

An aspect of the present invention is an architecture for computer aided detection capable of scaling up for increasing number of patients, and facilitates modifications and additions of CAD services based on various modalities. The present invention is a server configuration capable of providing services for determining a diagnosis upon being provided a set of medical images. The present invention is capable of being integrated into existing medical information systems.

An aspect of the present invention is a medical computer aided detection system, having a dispatcher for receiving one or more cases, each case including a set of medical image files, and distributing the files; an image processing server performing medical computer aided detection based on the set of medical image files using plug-in CAD components, the image processing server registering the plug-in CAD components with the dispatcher, the dispatcher distributing the medical image files based on the workload of the image processing server and the registered plug-in CAD components.

A system of the present invention can be expanded to include new or modified plug-in CAD components. In the system of the present invention, an Image Processing Server registers plug-in CAD components with the dispatcher. The dispatcher dispatches image files based on the availability of plug-in CAD components to perform detection services. By dispatching image files based on information of currently available CAD components, the system of the present invention can easily be expanded to accommodate new or modified plug-in CAD components.

An aspect of the image processing server of the medical computer aided detection system is execution of script files which invoke processing by plug-in CAD components in order to perform computer aided detection based on the medical image files. By invoking CAD components from script files, end users can easily add new or modified components to the system without knowledge of the details of the underlying CAD components and without having to re-compile other parts of the system.

An aspect of the system of the present invention is that each of the medical image files of the medical computer aided detection system contain a header including patient data, and image data. The medical image files processed by the system of the present invention can be used for detection without having to manage separate header files and without having to obtain information about the medical image data and associated patient from a separate source.

An aspect of the image processing server of the medical computer aided detection system is that it further determines if a script file has been pre-compiled or has been modified, if the script file has been modified, the image processing server determines if there is compiled version of the script, and if not, compiles the script file and executes the compiled script. Thus, the system of the present invention can handle compilation and execution of script files. This further simplifies the capability of expanding the system to accommodate new or modified CAD components.

An aspect of the image processing server of the medical computer aided detection system is that it includes an image service administrator and a script runner. The image server administrator registers plug-in CAD components with the dispatcher, and provided registered CAD components, creates a separate detection service process to manage execution of a script file and receives image files from the dispatcher. By creating a separate detection service process to manage execution of a scrip file, the system of the present invention can adapt to changes in demand for detection services. By managing execution of a script file with a separate service process, several service processes can be executed concurrently on a number of logic processors without affecting other service processes. Further, if a service process fails, the other executing service processes can continue execution. Accordingly, the present invention is adaptable to changes in demand and robust.

The medical image data contained in the medical image files of the medical computer aided detection system are based on modality and body part, and a script file is selected for conducting computer aided detection processing based on the type of modality. Thus, script files can be written based on modality to provide a detection service appropriate for the type of modality and body part. Furthermore, selection of the CAD components for performing detection based on medical image files can be made based on modality of the medical image data.

An aspect of the medical computer aided detection system is a capability to scale up to a greater number of patients and patient image files. In particular, the system of the present invention can include a plurality of image processing servers, wherein at least one image processing server of the plurality of image processing servers registers its plug-in CAD components upon startup, and wherein the dispatcher distributes image files of a case to an image processing server that is selected based on current work load and CAD components that have been registered with the dispatcher. By having added image processing servers register their available CAD services, the system of the present invention can easily add image processing servers.

An aspect of the image service administrator of the medical computer aided detection system is that it can further include a service associate that maintains a queue of detection service processes to be executed, and upon submitting a detection service process for execution obtained from the queue, informs the dispatcher of the change of workload status of the image processing server based on the number of detection processes currently in the queue and the number of detection processes being executed. By informing the dispatcher of the workload status of the image processing server, the dispatcher can dispatch medical image files based on the workload status of the image processing server.

A further aspect of the medical intelligent server for computer aided detecton is that if a plug-in CAD component is upgraded or newly added in an image processing server, the image processing server is re-started and registers the new set of CAD components with the dispatcher. By registering a new set of CAD components as CAD components are added or modified, dispatching of image files to an image processing server will be ensured of the most current capability of the image processing server. Furthermore, the medical intelligent server of the present invention is easily expanded to currently available CAD components.

DETAILED DESCRIPTION OF THE INVENTION

Figures 1, 4:
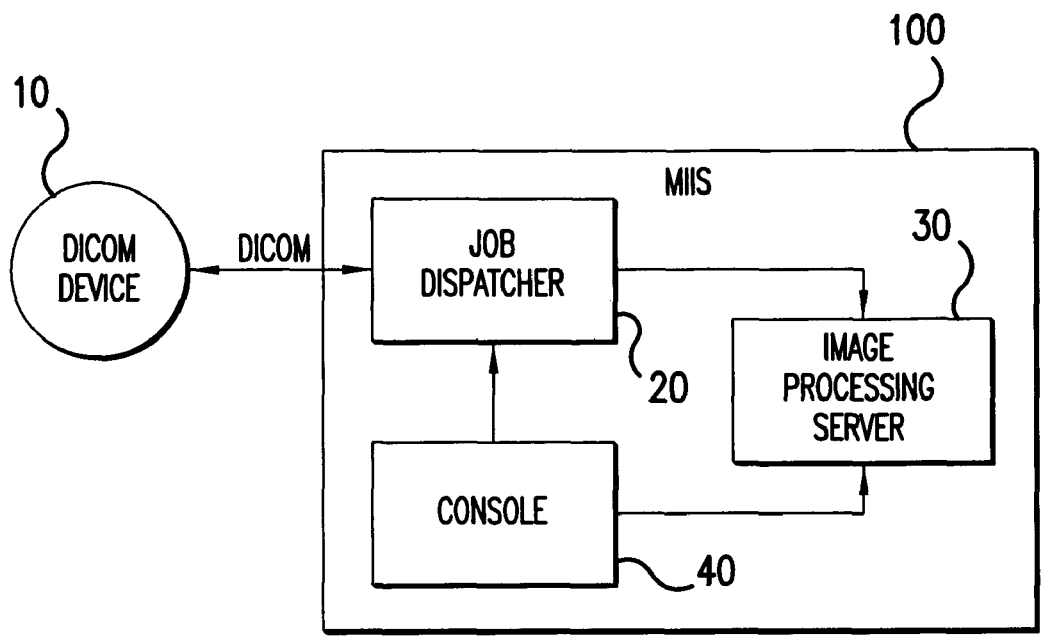
FIG. 1 shows a block diagram of the Medical Image Intelligence Server (MIIS) and interfaces.
FIG. 4 shows the format for a table of services provided in an Image Processing Server.

The present invention will be described in further detail with reference to the accompanying drawings.

The present invention can be used to help doctors and radiologists use advanced algorithms available for performing medical diagnosis. The present invention provides advanced CAD by sophisticated algorithms that accurately detect diseases such as cancer and subsequently provides valuable detection information. The present invention is designed to fit into existing medical information systems and workflows, as well as new hospital systems as it uses the DICOM standard communication protocol. Detection services are performed without significant delay. A built-in Web server enables 24/7 system access and report generation.

In particular, the present invention facilitates application of various CAD algorithms to a growing number of patients and patient images, and can be easily expanded to accommodate new and modified CAD services. The capability of handling greater capacity is facilitated by an architecture that is scalable to the number of concurrent patient case connections and the addition of servers to handle requested services over the patient case connections. The capability of expanding to new and modified CAD services is facilitated by scripts and plug-in service components. The present invention is dynamically adaptable to variations in demand for detection services.

DEFINITION OF TERMS AND ACRONYMS

The following definitions are provided for terms used throughout the description.

Association (DICOM protocol): a communication connection established between two DICOM applications by which DICOM information is exchanged. An association is preceded by initiation of a connection. An association is established by a process referred to as association negotiation.

Graphical User Interface (GUI): A program interface that takes advantage of the computers graphics capabilities to make the program easier to use. A user interface to a computer program that is considered an alternative to a GUI is a command-driven interface. Current GUI's have a pointer and associated pointing device that enables the user to select graphical objects on the display screen. GUI's can display functional components such as icons, menus, scroll bars that enable functions such as activating a command, or manipulating the display.

Message: a unit of information passed among running programs, devices, and within the operating environment. The unit of information can contain one or more blocks of text, control characters, a header, and error-checking or synchronization information.

Module: A collection of related application programs and service applications.

Server A computer or device on a network that manages resources and delivers service applications that can be used by other computers in the network.

Study (DICOM, also case): the DICOM term for a set of images of an image modality produced during a visit to a hospital, clinic, or other medical practice.

Task (also Process): A combination of a program being executed and bookkeeping information used by the operating system. When a program is executed by the computer, the operating system creates a new task for it. The task constitutes a wrapper for the program that identifies the program with a task number and attaches other bookkeeping information to it.

Transfer Syntax (from DICOM PS.3.5 2004): A set of encoding rules that allow Application Entities to unambiguously negotiate the encoding techniques (e.g., Data Element structure, byte ordering, compression) they are able to support, thereby allowing these Application Entities to communicate.

Windows Service (Microsoft): a highly specialized type of application designed to run for extended periods in its own Windows session. A Windows service typically runs as a background process, usually with no user interface, either locally or in a network. Most server-based applications, for example, are services. Windows services can be started from the Microsoft Management Console.

Modalities: CT, MR, CR, Ultrasound, and Nuclear Medicine systems, or imaging devices and equipment that send C-STORE requests (requests to store digital images in another system). Modalities have associated image modalities.

EXAMPLE MODALITIES

AS=Angioscopy
BI=Biomagnetic Imaging
CD=Color Flow Doppler
CP=Culposcopy
CR=Computed Radiography
CS=Cystoscopy
CT=Computed Tomography
DD=Duplex Doppler
DG=Diaphanography
DM=Digital Microscopy
DS=Digital Subtraction Angiography
DX=Digital Radiography
EC=Echocardiography
ES=Endoscopy
FA=Fluorescein Angiography
FS=Fundoscopy
HC=Hard Copy
LP=Laparoscopy
LS=Laser Surface Scan
MA=Magnetic Resonance Angiography
MR=Magnetic Resonance
MS=Magnetic Resonance Spectroscopy
NM=Nuclear Medicine
PT=Positron Emission Tomography (PET)
RF=Radio Fluoroscopy
RG=Radiographic Imaging (conventional film screen)
RTDOSE=Radiotherapy Dose
RTIMAGE=Radiotherapy Image
RTPLAN=Radiotherapy Plan
RTSTRUCT=Radiotherapy Structure Set
ST=Single-photon Emission Computed Tomography
TG=Thermography
US=Ultrasound
XA=X-Ray Angiography
XC=eXternal Camera
ECG=Electrocardiograms CAD (Computer Aided Detection): algorithms, for example pattern recognition algorithms, designed to detect regions in medical images that may be indications of diseases or illnesses.

DICOM: (Digital Imaging and Communications in Medicine). Is a comprehensive set of standards for handling, storing, printing and transmitting information in medical imaging. It includes file format definition and a network communications protocol. The protocol uses TCP/IP to communicate between systems. DICOM files can be exchanged between two entities that have the capability to receive the information—image and patient data—in DICOM format. See dicom.nema.org.

PACS: (Picture Archive and Communication System). Commercially available PACS provide an architecture that contains input modalities, a DICOM server, a PACS server, an Archive server, a Web server, a RIS (Radiology Information Server), and Radiology clients.

SOAP: (Simple Object Access Protocol).

A conceptual view of the Medical Image Intelligent Server (MIIS) of the present invention is shown in FIG. 1. As shown in FIG. 1, the MIIS is composed of a Job Dispatcher 20, a Console 40, and one or more Image Processing Servers 30 (only one shown for simplicity) The Job Dispatcher can establish a connection to one or more DICOM devices 10. DICOM devices include any DICOM compliant device, such as scanners, workstations, printers and network hardware.

The throughput requirement for large-scale hospital systems goes far beyond the capabilities that a single server can provide. The MIIS provides the capability to add more Image Processing Servers and coordinate their workload in order to reach suitable performance. The MIIS achieves scalability through the Job Dispatcher, which registers information of Image Processing Servers and dispatches images based on registered information, and expandability through the Image Processing Servers, which dynamically accommodate scripts for new or modified CAD services. The Job Dispatcher detects requests from DICOM devices, receives images for studies, and dispatches images to the appropriate Image Processing Server. The Job Dispatcher uses a Registration Service to carry out load balancing in an environment having an increasing number of new services, as well as modification of existing services.

The present invention discloses aspects of an Image Processing Server as the back-end of the MIIS. Details of the Job Dispatcher are disclosed in a related application (Attorney Docket No. 3352-0145PUS1), which as stated above is herein incorporated by reference.

Figure 2:
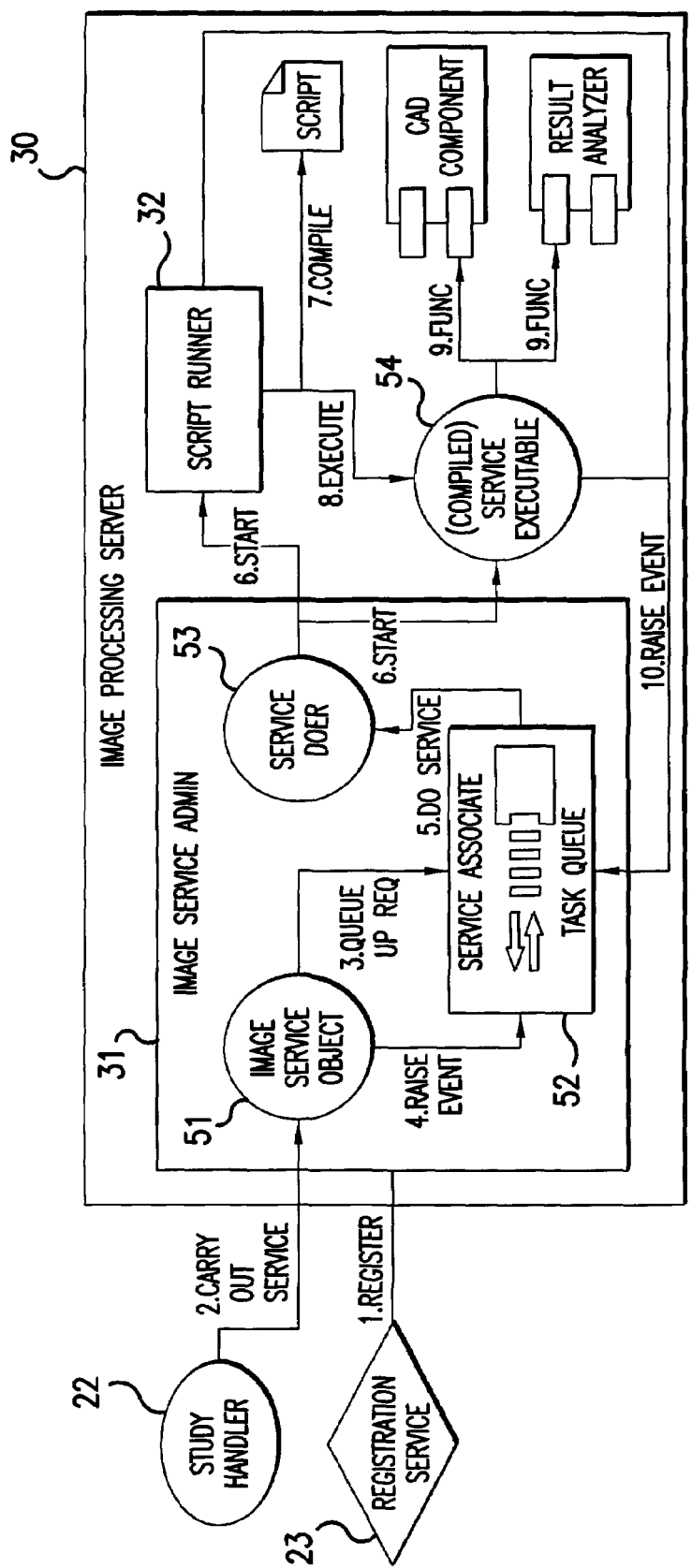
FIG. 2 shows a workflow diagram of an Image Processing Server.

FIG. 2 shows a workflow diagram of an Image Processing Server. The Job Dispatcher is capable of balancing workload among a large number of Image Processing Servers. As can be seen in FIG. 2, the Job Dispatcher includes a StudyHandler 22 and a Registration Service 23. An Image Processing Server can register ("Register") with the Registration Service 23. The Registration Service 23 stores and manages status information of Image Processing Servers 30. The status information includes a list of CAD services that the Image Processing Servers can provide, the process and protocol necessary to request a service by a Image Processing Server, and location of a Image Processing Server (e.g., local machine, or IP address).

An Image Processing Server must be registered with the Registration Service before it can be a member of a service group. The Job Dispatcher will retrieve registration information so that it can dispatch ("CarryOutService") images to an Image Processing Server for performing a CAD service. Registration information needs to be updated when the system configuration changes: for example, add/remove an Image Processing Server, or add/upgrade a CAD service.

An Image Processing Server 30 provides the CAD services of the MIIS. As shown in FIG. 2, an Image Processing Server 30 includes an Image Service Administrator 31, a Script Runner 32, and one or more plug-in CAD components 54. Script software programs combine one or more CAD image processing components together to carry out diagnosis based on DICOM images. CAD image processing components are wrapped into plug-in CAD components that expose methods that can be invoked by a script editor. Scripts are executed in a unit of project. A project is a file that describes the referenced assemblies and lists of script files in the project. Plug-in components exist that can analyze results and generate various formats of reports. Among the formats, the plug-in components have the capability to support DICOM and send DICOM images with results to designated locations. An example script is included in Appendix 1.

The Image Service Administrator 31 includes an Image Service Object 51, a Service Associate 52, and a Service Doer 53. The Image Service Object 51 provides methods for receiving images dispatched from the StudyHandler 22. Instances of the Image Server Object 51 are instantiated by the Image Service Administrator 31 on demand. Images received from the StudyHandler 22 are placed in a queue managed by the Service Associate 52.

The Service Associate 52 maintains a Service Doer queue that is ordered by priority and time that images are received (First-Come-First-Serve). The Service Associate 52 handles procedures that trigger events such as arrival of a new case, CAD service completed, and server shutdown. The Service Doer 53 obtains the image data and starts a child process to perform CAD image processing.

Figure 3:
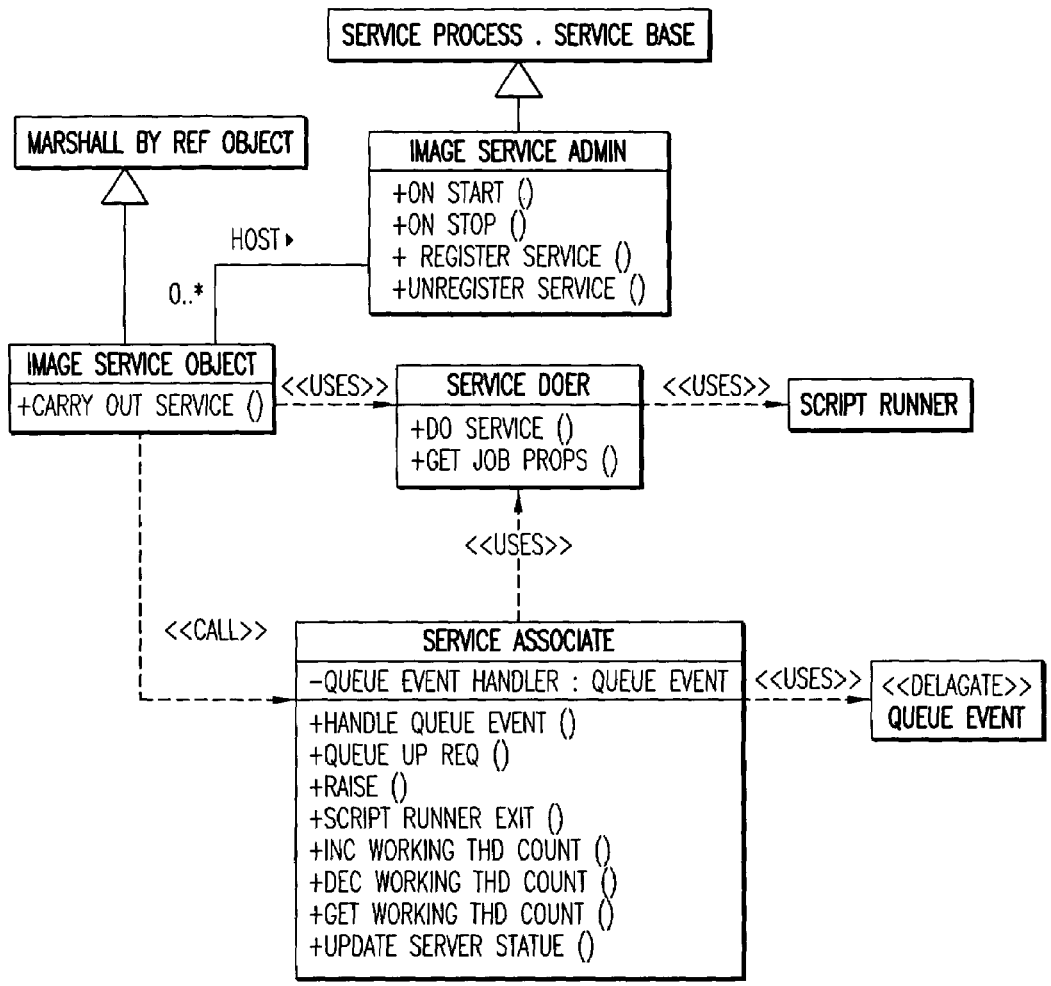
FIG. 3 shows a class diagram for the Image Service Administrator.

FIG. 3 shows a class diagram for the Image Service Administrator 31. The Image Service Administrator 31 includes an Image Server Admin class, an Image Service Object class, a Service Associate class, and a Service Doer class. Each class is shown with example methods that each instantiated object can perform. The Image Service Administrator 31, in an example embodiment, is a Windows service that runs continuously. The Image Service Administrator class includes an "OnStart" method, which when invoked, reads configuration settings and configures a Service Associate accordingly, loads an Image Service Object 51, calls a method "RegisterService" to register the Image Processing Server and services that it can process, and notifies the Service Associate that a service has started. The "RegisterService" method searches all image processing components and generates a summary table of services that the Image Processing Server can provide, or is currently executing, invokes a function to transfer the table of services with the remote Registration Service; 23. Each service in the table of services is preferably represented by a string "Modality/Bodypart." Services may be represented, for example as CR/BREAST, MG/BREAST, CR/CHEST, etc. The services represented in the table of services are preferably stored in a hash table (see FIG. 4). The Image Service Administrator 31 can also perform methods "OnStop" and "UnRegisterService." "OnStop" performs functions when services of the Image Processing Server 31 have discontinued, including the "UnRegisterService" function to un-register from the Register Service. The "Registration Service" method is also performed whenever a plug-in component is added or modified. Re-registration of an image processing server can be carried out by pausing or stopping the image processing server, upgrading the configuration and starting the image processing server and registering the new set of plug-in components.

The Image Service Object class contains a method "CarryOutService" that can be invoked by the StudyHandler to send images. Parameters include "Service Name" and image data, including DICOM headers and a flag indicating whether a request is a priority order. The "CarryOutService" is responsible for putting received data into an instance of a Server Doer object, push the Service Doer object into a queue in the Service Associate, and invoke a "Call Service Associate" method to raise an event, and notify the Service Associate that a new request has arrived.

The Service Associate 52 maintains a queue that holds requests. It contains methods that can be invoked to queue up a request and raise an event. It also provides a method to handle a raised event. In particular, the Service Associate contains a method "HandleQueueEvent" that delegates handling of a queue event. A method "QueueUpReq" takes an instance of Service Doer and its priority as parameters and pushes the Service Doer object into the queue. The method is invoked on a first-come-first-serve basis. However, if an object is set to priority, it will be inserted in top portion of the queue. The method "Raise" can be invoked to raise a queue event. The "HandleQueueEvent" mentioned above, takes two parameters as inputs: Sender—the object that sends the event, and QueueEventArg—the type of event that has been raised.

Queue event handling is based on the type of event raised. Example types of events include: arrival of a new request, image processing for a study has completed, a task has failed to execute, the Image Service Administrator has started, or has shut down. The Service Associate only allows a specific number of child processes to start for image processing at the same time. The value of this specific number is indicated in the configuration file of the Image Service Administrator. It can be automatically set to the number of logical processors available in a machine. In events related to a task, or arrival of a new request, the Service Associate checks the number of child processes currently running. If the number of child processes currently running is lower than a preset threshold, the next Service Doer object in the queue can be popped to execute; otherwise, the event is ignored. When a Service Doer object is popped to execute a task, to increase performance the Service Associate starts a separate child process, and runs "DoService" in the child process. When Image Service Administrator is shut down, a shutdown event will be fired and the Service Associate will stop running the child process and write all unfinished tasks into the hard drive. When the Image Service Administrator is started, a startup event is fired and all tasks written to the hard drive will be re-loaded and executed.

Other methods of the Service Associate that can be invoked include "ScriptRunnerExit," "IncWorkingThdCount," "DecWorkingThdCount," "GetWorkingThdCount," and "UpdateServerState." When the "ScriptRunnerExit" method is invoked due to an event received, the Service Associate raises a task done event and lets the queue event handler take over processing of the event. "IncWorkingThdCount," "DecWorkingThdCount," and "GetWorkingThdCount," maintain a count of the number of currently running child processes.

"UpdateServerState" is a method to provide information of the change in status of the Image Processing Server to the Registration Service. The status information can include the number of child processes started and the number of tasks in queue. The method is called when a new request handling event is raised, or can be called from inside the function "IncWorkingThdCount" or "DecWorkingThdCount."

As mentioned above, the Service Doer object is a holder for received data and images that is stored as a unit on a queue. The Service Doer object contains the method "DoService." Invoking the "DoService" method creates a separate child process to execute CAD image processing. The inventor of the present invention determined that a higher throughput can be achieved using an architecture that can accommodate a maximum number of image files at a time. Thus, the "DoService" method runs in the separate process so that a greater number of image files can be processed. Also, by running as a separate process, failure of the process will not affect other child processes, as well as the parent Image Processing Server.

The Service Doer also provides a method for returning a table listing the properties of the study stored in the Server Doer object. In particular, the method "GetJobProps," can be invoked by the Console to retrieve information about a case in queue or in process. The preferred list of properties that can be retrieved include:
Patient ID
Patient Name
Patient Sex
Accession Number
Modality of the study
Study Description
Study Date
Study Time
Referring Physician's Name The Scrip Runner 32 is an application invoked by Service Doer in the method "DoService." The Script Runner 32 is responsible for compiling, saving an assembly, and executing designated script files. Script files can make calls to CAD components and other plug-in components.

Figure 5:
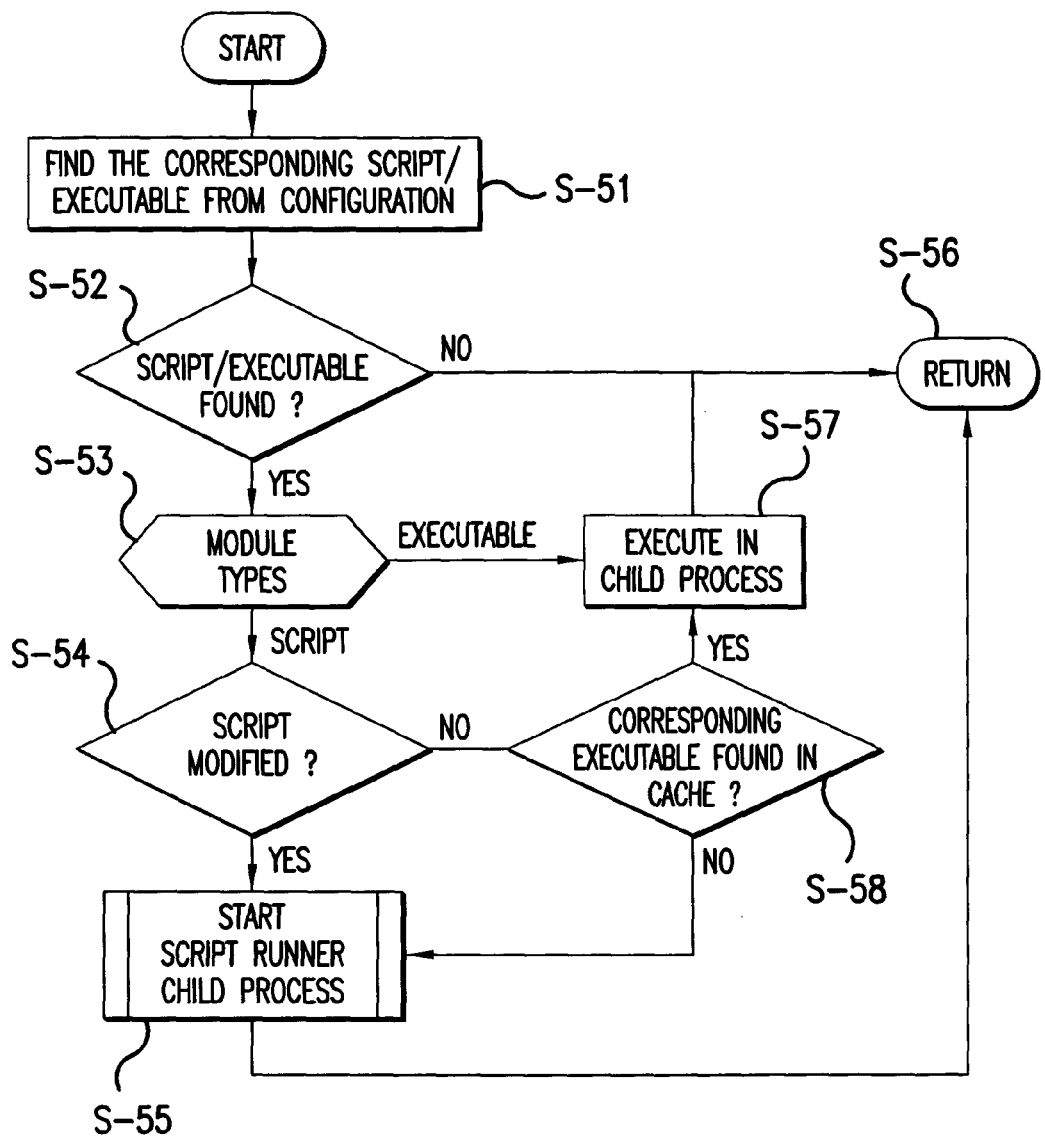
FIG. 5 shows a flow diagram of a Service Doer.

FIG. 5 shows a flow diagram of a Service Doer object. A child process of the Service Doer object is created and invoked to obtain a script for performing a requested detection service. The child process searches for a script, or corresponding executable, from the configuration of the Image Service Administrator (step S-51). If the desired script or executable is not found (step S-52: "No"), a message is sent to the Service Associate that the process has ended without results. If the desired script is found (step S-52: "Yes"), then one of two actions will be taken based on the type of module (step S-53). If the module is an executable, the executable is executed in the child process (step S-57). If the module is a script, a check is made as to whether the script has been modified (step S-54). If the script has not been modified (S-54: "No"), a check is made to locate a corresponding executable that may have been previously stored (step S-58). The executable, if found, is executed in the child process. If the script has been modified, the Script Runner is started to compile the script (step S-55). The compiled script is subsequently executed. A message is sent to the Service Associate when the process is completed, in order to enable processing of another script.

Plug-in CAD components are used by scripts by indicating what object and which method are invoked. Thus, plug-in components can be modified without re-compiling the entire server module in order to change the behavior of server objects. Also, script files can easily be prepared by end users without knowledge of the implementation details of plug-in components, and without extensive maintenance as plug-in components are revised over time. Through the use of scripts, the MIIS realizes a great deal of expandability.

Figure 6:
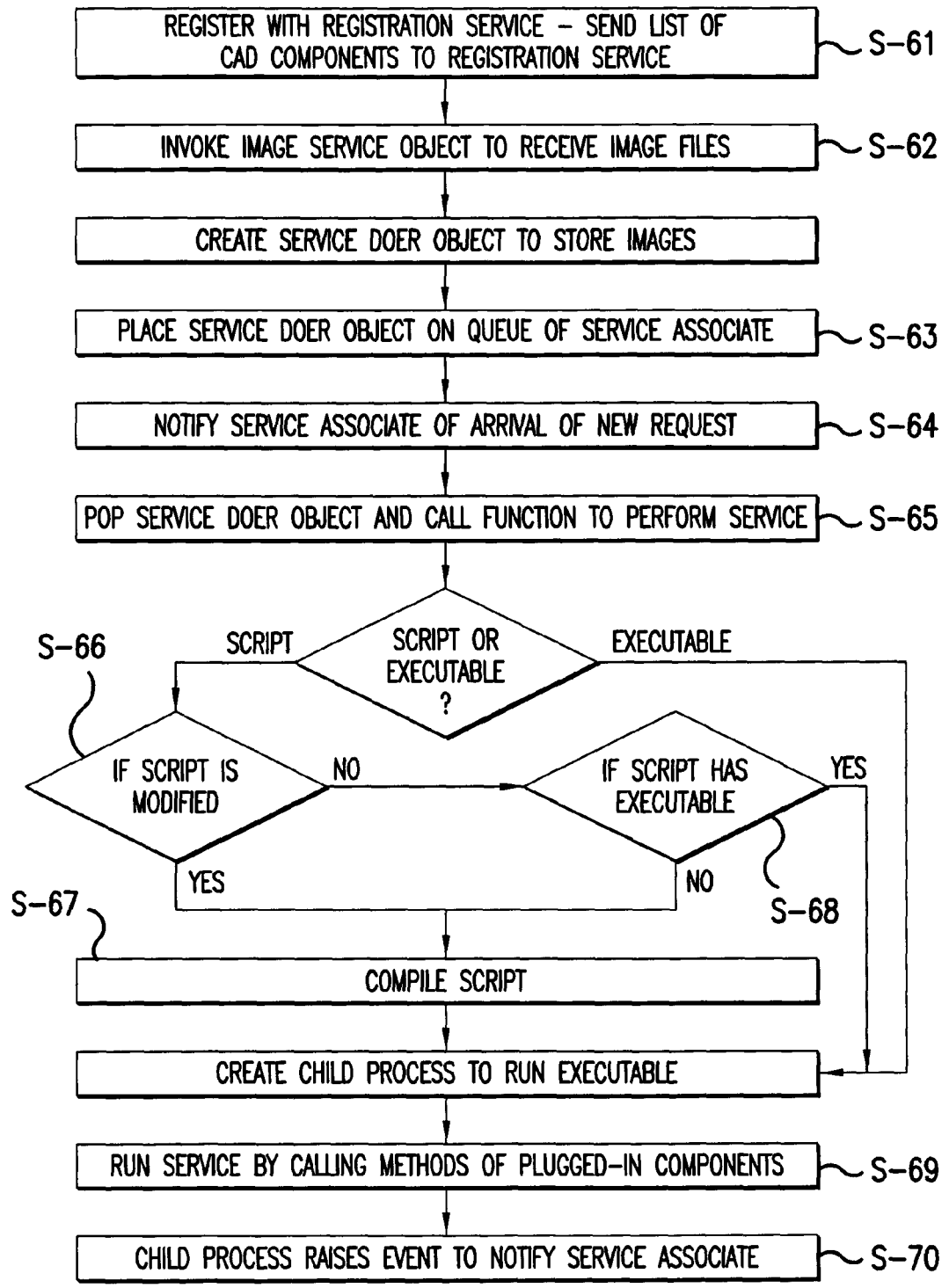
FIG. 6 shows a flow diagram for an example operation of the Image Processing Server.

FIG. 6 shows steps that may occur during a typical session in an Image Processing Server. The Image Processing System must first register with the Registration Service of the Job Dispatcher. The Image Service Administrator 31 is started and loads its configuration file. The Image Service Administrator 31 reviews all available image processing components that the Image Processing Server is capable of providing and summarizes the components in a service table.

The list of components is sent to the Registration Service that carries out a registration process. (Register, step S-61).

When the StudyHandler receives the images, it invokes an instance of Image Service Object 51 and calls the "CarryOutService" method to send the images. (CarryOutService, step S-62).

The Image Service Object 51 creates a Service Doer object 53, and calls the method "QueueUpReq" of the Service Associate 52. (QueueUpReq, step S-63). The Service Doer Object will be put into the queue that is maintained by the Service Associate.

The Image Service Object 51 raises an event to notify Service Associate 52 that a new request arrived. (Raise Event, step S-64). The Service Associate pops the Service Doer from the queue, and calls the DoService method to perform service as a separate process. (DoService, step S-65).

The Service Doer 53 starts the child process to perform a service. The Service Doer performs service in one of two ways. If a script file has been modified, or an executable is not available, the Script Runner 32 (Start, step S-66) compiles (Compile, step S-67) and runs the script. The compiled script will be saved to an executable for future use of the same script. If an executable is present, a child process is started to run the executable (Execute, step S-68). The executable runs by calling methods in plug-in components (Func, step S-69). When a service has completed, the child process raises an event to notify the Service Associate to process the next request stored in the queue (step S-70).

APPENDIX 1

```
/*
    FUJIFILM MIIS Sample Service Scripts
        version 1.0
    Copyright © 2006, FUJIFILM
    All rights reserved.
*/
public class Mammo
{
    public static int Main(string[ ] args)
    {
```

APPENDIX 1-continued

```
        // ...
        // objImgInfo: Images to be processed somewhere (get from
somewhere)
        // ...
        //==============================================
        // Process starts
        //==============================================
        Console.WriteLine("--------- Start Processing ---------");
        int iStatus = 0;
        try
        {
                ReportServiceAgent objAgent        = new
ReportServiceAgent( );
                MammoCad          objMammoCAD     = new MammoCad( );
                CadParam          objCADParam     = new CadParam( );
                CadResult         objCADResult    = new CadResult( );
                StorageOptions    objStorageOpts  = new
StorageOptions( );
                ImgResultOptions  objImgResultOpts = new
ImgResultOptions( );
                // Start CAD detection
                objCADParam.m_DetectType = "ALL";
                iStatus = objMammoCAD.CadDetect(objImgInfo,
objCADParam, objCADResult);
                // Put CAD results to DICOM SR, and sent them to PACSs
                objMammoCAD.SaveCadResultToSR(objImgInfo,
objCADResult, objStorageOpts);
                // Put CAD results into general image format (eg. jpg)
                objImgResultOpts.m_ImgType = "JPG";
                objMammoCAD.SaveCadResultToImg(objImgInfo,
objCADResult, objImgResultOpts);
                // Report results of service performed
                objAgent.UpdateServiceStatus(objImgInfo,
SVCSTATUS.SVC_SUCCESS);
        }
        catch(Exception e)
        {
                // Report failure of performed service
                objAgent.UpdateServiceStatus(objImgInfo,
SVCSTATUS.SVC_FAILED);
                Console.Out.WriteLine(e.ToString( ));
                if (iStatus == 0) iStatus = -1;
        }
        finally
        {
                Console.WriteLine("--------- Process Exiting. . . ---------");
        }
        return iStatus;
    } // end of Main
}
```

What is claimed is:

1. A medical intelligent server for computer aided detection (CAD), comprising:
a dispatcher for receiving one or more cases, each case including a set of medical image files, and distributing the files;
an image processing server performing medical computer aided detection based on the set of medical image files using plug-in CAD components, the image processing server registering the plug-in CAD components with the dispatcher, the dispatcher distributing the medical image files based on the workload of the image processing server and the registered plug-in CAD components; the medical intelligent server further comprising a plurality of image processing servers, wherein at least one image processing server of the plurality of image processing servers registers its plug-in CAD components upon startup, and wherein said dispatcher distributes image files of a case to an image processing server that is selected based on current work load and CAD components that have been registered with the dispatcher.

2. The medical intelligent server for computer aided detection of claim 1, wherein said image processing server executes script files which invoke processing by plug-in CAD components in order to perform computer aided detection based on the medical image files.

3. The medical intelligent server for computer aided detection of claim 2, wherein the image processing server determines if a script file has been pre-compiled or has been modified, if the script file has been modified, the image processing server determines if there is compiled version of the script, and if not, compiles the script file and executes the compiled script.

4. The medical intelligent server for computer aided detection of claim 1, wherein each of the medical image files contains a header including patient data, and image data.

5. The medical intelligent server for computer aided detection of claim 1, wherein the image processing server comprises an image service administrator and a script runner, the image server administrator registering plug-in CAD components with the dispatcher, and provided that the CAD components have been registered, creates a separate detection service process to manage execution of a script file based on the CAD components and receives image files from the dispatcher.

6. The medical intelligent server for computer aided diagnostic of claim 5, wherein the medical image files are based on modality and body part, and a script file is selected for conducting computer aided detection processing based on the type of modality.

7. The medical intelligent server for computer aided detection of claim 5, wherein the image service administrator comprises a service associate that maintains a queue of detection service processes to be executed, and upon submitting a detection service process for execution obtained from the queue, informs the dispatcher of the change of workload status of the image processing server based on the number of detection processes currently in the queue and the number of detection processes being executed.

8. The medical intelligent server for computer aided diagnostic of claim 1, wherein if a plug-in CAD component is upgraded or newly added in an image processing server, the image processing server is re-started and registers the new set of CAD components with the dispatcher.

* * * * *